United States Patent [19]

Pickenhagen et al.

[11] Patent Number: 4,889,735
[45] Date of Patent: Dec. 26, 1989

[54] FURANIC ESTERS AND THEIR UTILIZATION AS FLAVOR INGREDIENTS

[75] Inventors: Wilhelm Pickenhagen, Chavannes-Des-Bois, Switzerland; Alain Velluz, La Roche/Foron, France

[73] Assignee: Firmenich S.A., Geneva, Switzerland

[21] Appl. No.: 229,791

[22] Filed: Aug. 8, 1988

Related U.S. Application Data

[63] Continuation of Ser. No. 919,168, Oct. 15, 1986, abandoned.

[30] Foreign Application Priority Data

Nov. 5, 1985 [CH] Switzerland .......................... 4746/85

[51] Int. Cl.$^4$ ........................ A23L 1/226; A23L 1/235
[52] U.S. Cl. ..................................... 426/536; 131/277; 514/772; 549/477
[58] Field of Search ....................... 426/536; 131/277; 514/772; 549/477

[56] References Cited

U.S. PATENT DOCUMENTS 3,455,702  7/1969  Willhalm et al. ................... 426/536

4,127,592 11/1978  Cohen ............................... 549/477

FOREIGN PATENT DOCUMENTS 0167376  1/1986  European Pat. Off. ............ 549/477
2359891  6/1974  Fed. Rep. of Germany ...... 549/477
2910131  9/1980  Fed. Rep. of Germany ...... 426/556
2118954  8/1972  France .

Primary Examiner—Joseph Golian
Attorney, Agent, or Firm—Pennie & Edmonds

[57] ABSTRACT

Furanic esters of formula

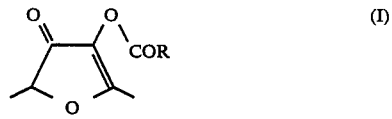

wherein R designates a linear or branched, saturated or unsaturated $C_2$–$C_6$ alkyl radical, are novel compounds having useful organoleptic properties and, consequently, can be used advantageously in the manufacture of flavor compositions, and in the aromatization of foodstuffs, beverages, pharmaceutical preparations and tobacco products.

5 Claims, No Drawings

FURANIC ESTERS AND THEIR UTILIZATION AS FLAVOR INGREDIENTS

This is a continuation of application Ser. No. 919,168 filed Oct. 15, 1986, now abandoned.

BRIEF SUMMARY OF THE INVENTION

The present invention relates to the field of aroma chemicals and more particularly it provides novel furanic esters of formula

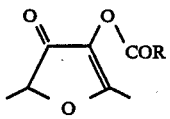

(I)

wherein R designates a linear or branched, saturated or unsaturated $C_2$–$C_6$ alkyl radical.

The instant invention relates also to the use of said compounds (I) as flavor ingredients to manufacture flavor composition and to confer, enhance or improve the organoleptic properties of foodstuffs in general, beverages and pharmaceutical preparations.

This invention provides further a flavor composition, a foodstuff, a beverage, a pharmaceutical preparation or a tobacco product containing as flavor effective ingredient a furanic ester of formula (I).

BACKGROUND OF THE INVENTION

The furanic esters of formula (I) belong to the family of 4-hydroxy-2,5-dimethyl-2,3-dihydrofuran-3-one, known in the art under its commercial name of FURANEOL (trademark of Firmenich SA, Geneva). Since its discovery, this compound has acquired wide acceptability in the trade and has become a critical ingredient not only for the reconstitution of strawberry flavors, but also as a constituent of a large variety of fruit flavors, or even meat aromas.

Numerous studies have been dedicated to this compound; however, surprisingly, sofar no attention has been directed to examine the organoleptic properties of its ester derivatives.

Swiss Patent No. 486,850, published on Apr. 30, 1970, mentioned that certain derivatives can decompose in situ to give Furaneol in foodstuff or beverages and that, consequently, can be used in place thereof. 2,5-Dimethyl-3-acetoxy-4-oxo-4,5-dihydrofuran is described as being one of these compounds.

DE-OS 23 59 891, published on June 6, 1974, describes certain esters of formula

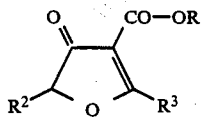

wherein R represents a $C_1$–$C_5$ alkyl radical, $R^2$ designates a $C_1$–$C_4$ linear or branched alkyl and $R^3$ stands for a hydrogen atom or a $C_1$–$C_7$ alkyl radical, as intermediates for the preparation of furanones.

No mention, nor suggestion has been formulated in the prior art concerning the flavoring properties of the esters of formula (I).

We have now discovered that the said esters possessed very useful aroma properties and that they could be used advantageously in the aromatization of various foodstuffs, beverages, pharmaceutical preparations and tobacco products.

THE INVENTION

The present invention is based on the fortuitous discovery that 2,5-dimethyl-4-oxo-3(5H)-furyl butanoate is present as a constituent in the absolute obtained from the extract of lyophilized strawberries wherein it is present in a concentration lower than about 70 ppm. This ester is therefore a compound of natural origin, the presence of which escaped sofar the attention of the numerous teams of investigators who had examined the composition of strawberry and fruit aromas.

The extract was obtained by a multistep process which consists in subjecting fresh strawberries to lyophilization, freezing them in liquid nitrogen and extracting with diethyl ether the powder obtained by grinding the freezed lyophilized fruits. After concentration, the ethereal extract was added of ethanol and kept under stirring at 40° C. for 30 minutes. The mixture was cooled to −7° C. and filtered while the alcohol was stripped off. The obtained residue was subjected to a separation by column chromatography on silica gel column by eluting with pentane and diethyl ether. 35 fractions were thus obtained, three of which only contained the ester in question. Its identity was later confirmed by comparison with a sample obtained by direct esterification of Furaneol with butyric anhydride. Though the flavor properties of 2,5-dimethyl-4-oxo-3(5H)-furyl butanoate are reminiscent of those of Furaneol, namely with respect to its caramel note, they differ from it with regard to its intensity, its enhanced buttery character and its lesser pronounced fruity note. Owing to its flavor characters and its strength, the said ester might constitute, according to the type of application, an ingredient of alternative or complementary use to Furaneol.

Besides, the compounds defined by formula (I), though characterized by only minor structural differences, show in actual experience more or less pronounced differences with respect to their flavor intensity and quality.

The following table summarizes the organoleptic characters of different esters of the invention.

| | Structure | Aromatic Quality |
|---|---|---|
| a. | 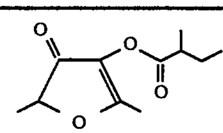 | fatty, plastic, slightly cheesy |
| b. | 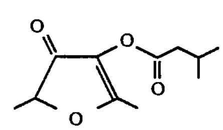 | buttery, anisic |
| c. | 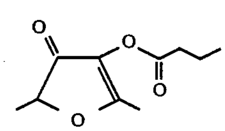 | caramel, strawberry, less fruity and more buttery than Furaneol |
| d. | 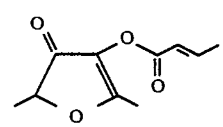 | metallic, less fruity than c. |

| Structure | Aromatic Quality |
|---|---|
| e. (structure) | fruity, more burnt than c. |
| f. (structure) | fatty, burnt, fruity, strawberry | a. 2,5-Dimethyl-4-oxo-3(5H)—furyl 2-methylbutanoate
b. 2,5-Dimethyl-4-oxo-3(5H)—furyl 3-methylbutanoate
c. 2,5-Dimethyl-4-oxo-3(5H)—furyl butanoate
d. 2,5-Dimethyl-4-oxo-3(5H)—furyl 2-butenoate
e. 2,5-Dimethyl-4-oxo-3(5H)—furyl pentanoate
f. 2,5-Dimethyl-4-oxo-3(5H)—furyl hexanoate It has become apparent that among the compounds of formula (I), 2,5-dimethyl-4-oxo-3(5H)-furyl butanoate was the compound which developed best the useful characters for the utilization according to the invention. However, the other analog esters of formula (I) can find a specific use according to the flavor effect sought and the nature of the product it is desired to aromatize.

The quality of the esters of the invention appear as absolutely surprising over the acquired knowledge of the art. The expert flavorist knows by experience that slight structural modifications lead, in most of the cases, to modifications in the organoleptic properties of a given compound, which modifications can often be regarded as fundamental. This situation occurs without any apparent rationale.

As often happens in analogous cases, the proportions of the esters of the invention required to produce the desired flavor effect can vary within a wide range. Their values will depend first on the type of flavor it is desired to reproduce, on the nature of the material it is desired to aromatize and on the nature of the coingredients present in a given flavor composition. Typically, these proportions are of the order of 1 to 100 parts per million (ppm), preferably of between about 5 to 20 ppm.

The esters are incorporated into the foodstuffs, beverages, pharmaceutical preparations and tobacco products at any given stage of their manufacture according to technics usual in the art, generally in admixture with other natural or synthetic flavor coingredients. Usually, they are added in the form of solutions in edible solvent such as triacetine, ethanol or propylene-glycol, or in admixture on a solid support, for instance on dextrin or gum arabic.

The term "foodstuff" as used herein is deemed to include a variety of edible material destined to human or animal consumption. The term include, but it is not limited to, ice-creams, desserts, yoghourts, milk products, confectionary or bakery articles, syrups, jams, toffees or gravies, solid concentrates for the preparation of soups, sauces or meat or meat-imitating products, such as meat extenders.

The term "tobacco" as used herein include natural tobaccos, such as burley, turc or Maryland tobacco, as well as artificial and reconstituted or homogenized tobacco. The shaped articles manufactured by using such tobaccos can be indifferently smoking articles or chewing and sniffing products.

The esters of the invention can easily be prepared by a simple process of esterification of Furaneol. Depending on the specific esters desired, this can occur by using the anhydride or the halide of the appropriate carboxylic acid according to the following reaction scheme:

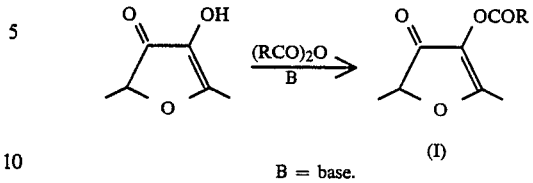

B = base.

The process followed is known by itself and the specific method employed will be illustrated by the following examples. In the following section, certain specific applications will also be described; the invention, however, will not be limited thereto. Temperatures are given in degrees centigrade and the abbreviations have the meaning common in the art.

EXAMPLE 1

2,5-Dimethyl-4-oxo-3(5H)-furyl butanoate

158 G (1M) of butyric anhydride were introduced dropwise at 0°–3° under nitrogen and with vigorous stirring into a mixture of 128 g (1M) of FURANEOL (commercial product of Firmenich SA) and 385 g (4, 9M) of pyridine. The reaction mixture was kept under stirring while the temperature raised to room temperature. The mixture was then extracted with 100 ml of ether and the ethereal extract was subjected to the usual treatments of neutralization with two fractions of 25 ml each of a 10% aqueous NaOH solution, washing with a saturated aqueous solution of NaCl and drying over MgSO$_4$. The evaporation under vacuum of the solvent gave a residue which upon distillation with a Vigreux column yielded 123 g of the desired product having b.p. 70°/11.6 Pa.

EXAMPLE 2

2,5-Dimethyl-4-oxo-3(5H)-furyl 2-methyl-butanoate 5.28 G (0.044M) of 2-methyl-butanoyl chloride were added dropwise at 0°–3° under nitrogen and with stirring to a mixture of 5.12 g (0.04M) of FURANEOL and 12.8 ml (0.2M) of pyridine. After having left the temperature raising to the room temperature, the mixture was treated with 50 ml of ether. As indicated in Example 1, the ethereal extract was subjected to the usual treatments. The residue obtained after evaporation of the solvent was distilled under vacuum in a bulb apparatus to give the desired ester having b.p. 87°/12 Pa.

By following one of the general methods indicated above, the esters described hereinbelow were prepared. In the table which follows are summarized the analytical data (IR, NMR, MS) corresponding to each of the compounds thus prepared.

a. 2,5-Dimethyl-4-oxo-3(5H)-furyl 2-methyl-butanoate ($C_{11}H_{16}O_4$)

NMR (CDCl$_3$): 1.0 (3H, t); 1.26 (3H, d); 1.49 (3H, d); 1.6 (1H, m); 1.79 (1H, m); 2.15 (3H, s); 2.62 (1H, m); 4,57 (1H, q) delta ppm;

IR (CHCl$_3$): 2960, 2930, 2870, 1755, 1705, 1630, 1300, 1185, 1135, 1100, 995 cm$^{-1}$;

MS: M$^+$=212 (8); m/e: 41 (11), 43 (28), 57 (100), 72 (10), 85 (73), 128 (38), 129 (16).

b. 2,5-Dimethyl-4-oxo-3(5H)-furyl 3-methylbutanoate ($C_{11}H_{16}O_4$)

NMR (CDCl$_3$): 1.04 (6H, d); 1.5 (3H, d); 2.16 (3H, s); 2.19 (1H, m); 2.41 (2H, d); 4.56 (1H, q) delta ppm;

IR (CHCl$_3$): 2990, 2955, 2900, 1770, 1720, 1645, 1315, 1195, 1150, 1100, 1010 cm$^{-1}$;

MS: M$^+$=212 (11); m/e: 39(6), 41 (22), 43 (47), 57 (100), 72 (9), 85 (87), 128 (75), 129 (11).

c. 2,5-Dimethyl-4-oxo-3(5H)-furyl butanoate (C$_{10}$H$_{14}$O$_4$)

NMR (CDCl$_3$): 1.01 (3H, t); 1.49 (3H, d); 1.74 (2H, m); 2.16 (3H, s); 2.52 (2H, t); 4,56 (1H, q) delta ppm;

IR (CHCl$_3$): 2960, 2930, 2875, 1760, 1710, 1630, 1305, 1185, 1135, 1095, 995 cm$^{-1}$;

MS: M$^+$=198 (7); m/e: 41 (9), 43 (100), 57 (11), 71 (51), 72 (11), 85 (33), 128 (54).

d. 2,5-Dimethyl-4-oxo-3(5H)-furyl 2-butenoate (C$_{10}$H$_{12}$O$_4$)

NMR (CDCl$_3$): 1.51 (3H, d); 1.75 (3H, d); 2.17 (3H, s); 4,58 (1H, q); 6,01 (1H, d); 7,18 (1H, dxq) delta ppm;

IR (CHCl$_3$): 2990, 2925, 1735, 1700, 1625, 1300, 1285, 1185, 1145, 1095, 995, 960 cm$^{-1}$;

MS: M$^+$=196 (4); m/e: 41 (16), 43 (9), 69 (100), 128 (9).

e. 2,5-Dimethyl-4-oxo-3(5H)-furyl pentanoate (C$_{11}$H$_{16}$O$_4$)

NMR (CDCl$_3$): 0,95 (3H, t); 1.43 (2H, m); 1.5 (3H, d); 1.7 (2H, m); 2.16 (3H, s); 2.54 (2H, t); 4,57 (1H, q) delta ppm;

IR (CHCl$_3$): 2955, 2930, 2875, 1760, 1705, 1630, 1415, 1300, 1185, 1135, 995 cm$^{-1}$;

MS: M$^+$=212 (4); m/e: 41 (19), 43 (31), 55 (14), 57 (100), 72 (11), 85 (93), 128 (66).

f. 2,5-Dimethyl-4-oxo-3(5H)-furyl hexanoate (C$_{12}$H$_{18}$O$_4$)

NMR (CDCl$_3$): 0,92 (3H, t); 1.36 (4H, m); 1.5 (3H, d); 1.72 (2H, m); 2.16 (3H, s); 2.53 (2H, t); 4,57 (1H, q) delta ppm;

IR (CHCl$_3$): 2955, 2925, 2870, 1760, 1705, 1630, 1300, 1185, 1135, 1095, 995 cm$^{-1}$;

MS: M$^+$=226(3); m/e: 41 (11), 43 (100), 55 (17), 57 (10), 71 (69), 72 (15), 85 (35), 99 (51), 128 (76), 129 (11).

EXAMPLE 3

Flavor comparison

A comparison of the flavor qualities of 2,5-dimethyl-4-oxo-3(5H)-furyl butanoate with those developed by FURANEOL was carried out by examining a sample of the products in question at a level of 20 ppm in mineral water. The comments expressed by a panel of expert flavorists are summarized hereinbelow:

FURANEOL: typical caramel, fruity, slightly burnt, sweet, strawberry 2,5-dimethyl-4-oxo-3(5H)-furyl butanoate: caramel, less fruity than FURANEOL, more buttery, less powerful.

A similar comparison was carried out on samples of each of the esters of the invention and the results observed are summarized above in the description of the specification.

EXAMPLE 4

Fruity flavoring composition

A flavor base composition of fruity pineapple type was prepared by mixing the following ingredients (parts by weight):

| | |
|---|---|
| Vanillin | 3.0 |
| Conc. orange oil extract | 5.0 |
| Conc. lemon oil extract | 10.0 |
| Ethyl butyrate | 10.0 |
| Ethyl hexanoate | 0.5 |
| Allyl hexanoate | 12.0 |
| Ethyl isovalerianate | 3.0 |
| Isoamyl acetate | 0.5 |
| 10% alpha-Ionone* | 0.5 |
| Ethyl oenanthate | 1.0 |
| 95% Ethanol (v/v) | 54.5 |
| | 100.0 |

*in 95% ethanol

By using the above base, two separate compositions were prepared as follows:

| | Aroma A | Aroma B |
|---|---|---|
| 2,5-Dimethyl-4-oxo 3(5H)—furyl butanoate | — | 0.5 |
| Pineapple base | 10.0 | 10.0 |
| 95% Ethanol | 90.0 | 89.5 |
| | 100.0 | 100.0 |

The resulting compositions were subjected to evaluation in an acidic sugar solution (10% saccharose and 0.10% of citric acid in mineral water) at a concentration level of 0.10%.

The expert flavorists, members of the evaluation panel, defined that Flavor B was fuller, sweeter, more harmonious and natural than Flavor A; it possessed moreover a more characteristic pineapple character.

EXAMPLE 5

Fruity flavoring composition

A base flavor composition of fruity strawberry-type was prepared by mixing the following ingredients (parts by weight):

| | |
|---|---|
| Ethyl butyrate | 3.5 |
| Ethyl methylphenylglycidate | 0.7 |
| cis-3-Hexenol | 0.5 |
| 10% Isobutyl acetate* | 3.5 |
| 10% Styrallyl acetate* | 1.5 |
| 10% Ethyl 2-methylbutyrate* | 1.0 |
| gamma-Decalactone | 0.5 |
| 10% Methyl-cinnamate* | 10.0 |
| 95% Ethanol (v/v) | 78.8 |
| | 100.0 |

*in 95% ethanol

By using the above base, two separate compositions were prepared as follows:

| | Aroma A | Aroma B |
|---|---|---|
| 2,5-Dimethyl-4-oxo 3(5H)—furyl butanoate | — | 0.7 |
| Strawberry base | 10.0 | 10.0 |
| 95% Ethanol | 90.0 | 89.3 |
| | 100.0 | 100.0 |

The resulting compositions were evaluated in terms of their flavor characters in an acidic sugar solution (10% saccharose and 0.10% citric acid in mineral water) at a concentration level of 0.10%.

The expert flavorists defined Flavor B as being more ripe, more fruity and slightly more buttery than Flavor A; it possessed moreover a more pronounced strawberry character. Flavor A showed, on the contrary, a greener note.

EXAMPLE 6

Flavor composition of butter type

A flavor composition of butter type was prepared by mixing the following ingredients (parts by weight):

| | |
|---|---|
| Vanillin | 1.5 |
| Diacetyl | 3.0 |
| Acetylmethyl carbinol | 10.0 |
| Butyric acid | 15.0 |
| 10% gamma-Octalactone* | 2.5 |
| Ethyl butyrate | 10.0 |
| 1% gamma-Undecalactone* | 10.0 |
| Vegetable oil(1) | 48.0 |
| | 100.0 |

*in 95% ethanol
(1)fraction of coconut oil

By using the above base composition, two separate compositions were prepared as follows:

| | Aroma A | Aroma B |
|---|---|---|
| 2,5-Dimethyl-4-oxo 3(5H)—furyl butanoate | — | 0.5 |
| Butter base | 10.0 | 10.0 |
| Vegetable oil (vide supra) | 90.0 | 89.5 |
| | 100.0 | 100.0 |

Biscuits of soft dough were prepared by mixing the following ingredients (parts by weight):

| | |
|---|---|
| Sugar, confectioner | 210 |
| Margarine | 175 |
| Sugar syrup (65%) | 40 |
| Skimmed milk powder | 30 |
| Eggs powder | 20 |
| Flavor (A or B) | 38 |
| Flour | 600 |
| Salt | 6 |
| Ammonium bicarbonate | 7 |
| Sodium bicarbonate | 6 |
| Water | 180 |
| | 1312 |

(The first five ingredients form mixture X.)

The flavor was added in the form of a premix in the sugar syrup to mixture X constituted by the material, the syrup and the sugar, in order to obtain a good diffusion within the dough.

The obtained mixture containing the flavor was intimately mixed for 3 min in a suitable apparatus, then the other ingredients were added while mixing for 3 other min.

The soft dough was then pressed on a rotary drum and deposited on molds of 3 mm thickness. The biscuits were slightly dusted with sugar before cooking. This was effected in a laboratory rotary baking oven at a temperature of 210°, the first minute with steam injection.

The experts unanimously found that the biscuits flavored with Flavor B possessed a flavor and taste richer and fuller than those flavored with Flavor A; they showed moreover a more pronounced "baked" character.

EXAMPLE 7

Aromatization of a meaty product

A reconstituted beef soup was prepared by mixing the following ingredients (parts by weight):

| | |
|---|---|
| Commercial beef extract | 10 |
| Monosodium glutamate | 1 |
| 50/50 Mixture of sodium inositate and sodium guanilate | 0.005 |
| Sodium chloride | 8.0 |
| Lactic acid | 0.5 |
| Water | 980.495 |
| | 1000.0 |

The resulting soup was then divided into two portions of equal volume and to one of them, there was added 2,5-dimethyl-4-oxo-3(5H)-furyl butanoate at a concentration of 2 ppm. The fraction thus flavored was then subjected to an organoleptic evaluation by comparison with unflavored fraction.

The general opinion expressed by the flavorists, members of the evaluation panel, was that the flavored soup possessed a richer and fuller taste with a slightly roastier and more juicy tonality than the unflavored soup.

What we claim is:

1. Pure compounds of formula (I)

wherein R represents a linear or branched, saturated or unsaturated $C_2$-$C_6$ alkyl radical.

2. Pure 2,5-Dimethyl-4-oxo-3(5H)-furyl butanoate.

3. Method to confer, improve or enhance the flavor quality of foodstuffs, beverages, pharmaceutical preparations and tobacco products, which comprises adding thereto a small but flavor effective amount of a compound according to claim 1.

4. Flavoring composition containing as active ingredient a compound according to claim 1.

5. A foodstuff, a beverage, a pharmaceutical preparation or a tobacco product containing as active flavor ingredient a compound according to claim 1.

* * * * *